United States Patent [19]

Morita et al.

[11] 4,164,577

[45] Aug. 14, 1979

[54] 6-(2-ACYLAMINO-2-ARYLACETAMIDO)-PENICILLANIC ACIDS

[75] Inventors: Yoshiharu Morita, Yokohama; Junichi Ohya, Zama; Tadashi Shirasaka, Yokohama, all of Japan

[73] Assignee: Mitsubishi Chemical Industries, Ltd., Tokyo, Japan

[21] Appl. No.: 880,132

[22] Filed: Feb. 22, 1978

[30] Foreign Application Priority Data

Apr. 4, 1977 [JP] Japan .................................. 52-38227

[51] Int. Cl.$^2$ ................... A61K 31/43; A61K 31/165; C07D 499/68

[52] U.S. Cl. ...................................... 424/251; 424/250; 424/271; 260/239.1

[58] Field of Search ..................... 260/239.1; 424/271, 424/250, 251

[56] References Cited

U.S. PATENT DOCUMENTS

| | | | |
|---|---|---|---|
| 3,433,784 | 3/1969 | Long et al. | 260/239.1 |
| 3,992,371 | 11/1976 | Tobiki et al. | 260/239.1 |

Primary Examiner—Gerald A. Schwartz
Attorney, Agent, or Firm—Stevens, Davis, Miller & Mosher

[57] ABSTRACT

6-(2-acylamino-2-arylacetamido)penicillanic acids are prepared and shown to be useful as antibacterial agents.

16 Claims, No Drawings

6-(2-ACYLAMINO-2-ARYLACETAMIDO)PENICILLANIC ACIDS

BACKGROUND OF THE INVENTION

1. Field of the Invention

This invention relates to 6-(2-acylamino-2-arylacetamido) penicillanic acids which are effective against Gram-negative and Gram-positive bacteria.

2. Description of the Prior Art

While many penicillins have been remarkably effective in the treatment of a variety of infections, few penicillins have been found to possess significant activity against *Pseudomonas aeruginosa*. There is a continuing need for different and improved penicillins.

SUMMARY OF THE INVENTION

Accordingly, it is an object of this invention to provide novel 6-(2-acylamino-2-arylacetamido)penicillanic acids having superior antibacterial activity. This and other objects of the present invention as will hereinafter become clear have been attained by providing compounds of the formula (I):

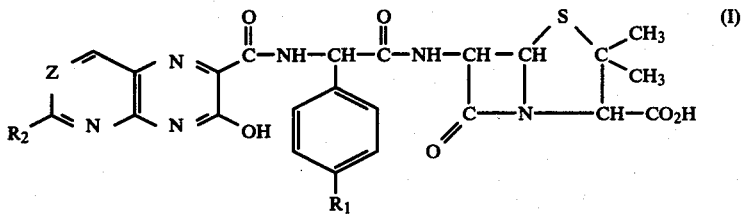

wherein $R_1$ is hydrogen or hydroxy; $R_2$ is hydrogen, methyl or ethyl; and Z is —CH=, —N= or —CX= wherein X is chloro or bromo.

Also encompassed within this invention are non-toxic, pharmaceutically acceptable salts thereof.

DETAILED DESCRIPTION OF THE PREFERRED EMBODIMENTS

As summarized above, this invention relates to a group of compounds useful as antibacterial agents, which compounds are represented by Formula I above.

Also included within the scope of this invention are the non-toxic cationic, e.g., the pharmaceutically acceptable salts of the compounds of this invention. Such salts include, for example, sodium, potassium, calcium, magnesium, ammonium and substituted ammonium salts, e.g., procaine, N,N'-dibenzylethylenediamine.

As one skilled in the art can readily appreciate, the compounds of this invention are sufficiently basic, by virtue of the nitrogen-containing heterocyclic ring, to form acid addition salts; said salts, especially the pharmaceutically acceptable acid addition salts, are also considered within the scope of this invention. Such salts include, for example, inorganic salts such as hydrochlorides and sulfates, and organic salts such as fumarates, malates and formates.

PREPARATION

The preparation of the compounds of this invention involves coupling of a 6-(2-amino-2-arylacetamido)-penicillanic acid and a carboxylic acid having the formula (II):

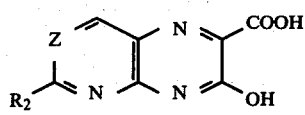

wherein $R_2$ and Z are as defined herein above, by the reaction of the carboxy function of the carboxylic acid with the amino function of the 6-(2-amino-2-arylacetamido) penicillanic acid to produce an amide linkage.

The compounds of this invention can be prepared by the reaction of the carboxylic acid with the appropriate 6-(2-amino-2-arylacetamido)penicillanic acid in the presence of a condensing agent, e.g., a carbodiimide such as 1,3-dicyclohexylcarbodiimide. Excess carbodiimide is converted to the corresponding urea by acidification, the pH is adjusted to near neutrality and the urea is removed by filtration. The products may be recovered by acidification or extraction.

In rendering the carboxy function active to the coupling reaction, the carboxy function is converted to an acid halide, acid azide, activated ester (e.g., p-nitrophenyl ester) or mixed carbonic anhydride, or imidazolide through the use of N,N'-carbonyldiimidazole. These acylating agents need not be isolated. It is frequently more convenient and practical to use them in the form of the solution, in which they are prepared.

The conversion of the carboxylic acid to a mixed carbonic anhydride is effected by dissolving the carboxylic acid in a ketone solvent containing a tri-(lower)alkylamine and treating the solution with an anhydride forming reagent, e.g., a lower alkyl chloroformate or an aryl chloroformate at a temperature of from 0° to —20° C. The compounds of this invention are obtained by reacting the mixed anhydride with the 6-(2-amino-2-arylacetamido)penicillanic acid at a temperature of about —50° to +50° C. Recovery of the product is effected by precipitation (after acidification of the reaction mixture) or by extraction into an organic solvent such as ethyl acetate, methyl isobutyl ketone or the like, from an acidified reaction mixture.

The particular methods of coupling employed in preparing the compounds of this invention are each now well recognized in the art. The conditions under which a particular coupling reaction would be carried out will be apparent to those skilled in the art.

The 6-(2-acylamino-2-arylacetamido)penicillanic acids of this invention are remarkably effective in treating a number of infections caused by Gram-negative bacteria including *Esherichia coli, Proteus vulgaris, Pseudomonas aeruginosa*, and Gram-positive bacteria including *Staphylococcus aureus*. As described above, the compounds of this invention exhibit antibacterial activity against microorganisms. Their useful activity can be demonstrated by in vitro tests against various organisms.

The compounds of this invention were tested for antibacterial activity according to the following procedure.

Nutrient broth and nutrient agar were prepared according to the conventional procedure. Nutrient agar was used as a vehicle. The stock solution was prepared at 100 μg/ml of the test material in the vehicle. Two-fold dilutions were made with the vehicle and then the diluted stock solution was added to a petri dish and solidified by chilling. Test organisms were grown in the nutrient broth for 20 hours at 37° C. The hardened surface was inoculated with a loopful of the test organism solution containing $1 \times 10^6$ cells per milliliter and incubated for 20 hours at 37° C. At the end of this period, growth of the organism was observed. The minimum inhibitory concentration (MIC) at which growth of the organism failed to occur was observed and recorded. The following Table 1 summarizes the activity of representative compounds as active antibacterial agents, and compares them with the reference drug Sulbenicillin.

TABLE 1

Compound:

$$R-\overset{O}{\underset{}{C}}-NH-CH(-C_6H_4-R_1)-\overset{O}{\underset{}{C}}-NH-CH-CH\overset{S}{\underset{N-CH-CO_2K}{\diagdown}}C(CH_3)_2$$

| No. | R | $R_1$ | Minimum Inhibitory concentration (MIC: μg/ml) Pseudomonas aeruginosa M-12* | Pseudomonas aeruginosa M-16* | Pseudomonas aeruginosa M-2008** |
|---|---|---|---|---|---|
| 1 | (1,8-naphthyridin-2-yl)-C(OH)= | H | 3.1 | 1.5 | 6.2 |
| 2 | (1,8-naphthyridin-2-yl)-C(OH)= | OH | <1.5 | 0.78 | 3.1 |
| 3 | 6-Cl-(1,8-naphthyridin-2-yl)-C(OH)= | H |  | <1.5 | 6.2 |
| 4 | 6-Cl-(1,8-naphthyridin-2-yl)-C(OH)= | OH |  | 3.1 | 6.2 |
| 5 | 6-Br-(1,8-naphthyridin-2-yl)-C(OH)= | H |  | <1.5 | 6.2 |
| 6 | 6-Br-(1,8-naphthyridin-2-yl)-C(OH)= | OH |  | <1.5 | 3.1 |
| 7 | (pyrazino-pyridyl)-C(OH)= | H |  | <1.56 |  |
| 8 | (pyrazino-pyridyl)-C(OH)= | OH |  | <1.56 |  |
| 9 | Br,CH$_3$-(naphthyridinyl)-C(OH)= | H |  | 3.1 |  |
| 10 | Br,CH$_3$-(naphthyridinyl)-C(OH)= | OH |  | 1.5 |  |
| 11 | Sulbenicillin |  | 25 | 25 | 25 |

*A mutant derived from Pseudomonas aeruginosa (ATCC 15692)
**A mutant derived from Pseudomonas aeruginosa (ATCC 15691)

In general, the compounds of this invention may be utilized in a manner similar to ampicillin and other penicillins. For example, they may be used in various animal species in an amount of about 0.1 to 100 mg/kg daily, orally or parenterally in two to five divided doses to treat infections of bacterial origin.

Having generally described the invention, a more complete understanding can be obtained by reference to certain specific examples, which are included for purposes of illustration only and are not intended to be limiting unless otherwise specified.

EXAMPLE

To a suspension of 382 mg (2 m moles) of 3-hydroxypyrido [2,3-b]pyrazine-2-carboxylic acid in 12 ml of dry dimethylformamide was added 365 mg (2.2 m moles) of N,N'-carbonyldiimidazole. The mixture was stirred for 1.5 hours in an ice bath. To this mixture was added a solution of 838 mg (2 m moles) of amoxycillin trihydrate in 5 ml of dimethylformamide and 0.278 ml (2 m moles) of triethylamine. The reaction mixture was stirred for 3 hours at room temperature. To the resultant homogenous solution was added 690 mg (2.22 m moles) of 59% potassium 2-ethylhexanoate-n-butanol solution and then the solution was poured into 150 ml of acetone to give a precipitate, which was filtered, dissolved into 100 ml of water, adjusted to pH 2.0 and then extracted twice with ethyl acetate (100 ml, 50 ml). The ethyl acetate layer was washed twice with 40 ml of water, dried over anhydrous magnesium sulfate and then adjusted to pH 7.0 with potassium 2-ethylhexanoate-n-butanol solution to yield crystals. This was filtered, washed with ether and then dried to give 443 mg of potassium 6-[D-2-(3-hydroxypyrido[2,3-b]pyrazine-2-carboxamido)-2-(p-hydroxyphenyl)acetamido]-penicillanate, M. P.>250° C.

Analysis - Calcd. for $C_{24}H_{21}O_7N_6S_1K_1$ (percent): C, 49.99; H, 3.67; N, 14.58; S, 5.56 Found (percent): C, 47.25; H, 4.22; N, 12.48; S, 5.76

IR (KBr): 3,400, 3,280, 1,760, 1,635, 1,590, 1,510, 1,455, 1,420 and 1,260 $cm^{-1}$ NMR ($D_2O$), (100 MHz), δ(ppm): 1.43 (s, 3H), 1.47 (s, 3H), 4.21 (s, 1H), 5.40–5.72 (m, 3H), 6.80–7.06 (m, 2H), 7.24–7.56 (m, 3H), 8.22 (q, 1H), 8.56 (q, 1H)

Various other 6-(2-acylamino-2-arylacetamido)-penicillanic acids were synthesized in accordance with the procedure of the above example, and the results are summarized in the following Table 2.

TABLE 2

Compound

R—C(O)—NH—CH(Ar-$R_1$)—C(O)—NH—CH—CH(S)(C(CH_3)_2)—CH—$CO_2K$ (penicillanate structure)

| No. | R | $R_1$ | Yield (%) | m.p. (°C.) | IR (KBr) (cm$^{-1}$) | NMR (100 MHz) δ(ppm) |
|---|---|---|---|---|---|---|
| 1 | pyrido[2,3-b]pyrazin-2-yl-3-OH | H | | 240–250 | 3400, 1760, 1640, 1595, 1505, 1455, 1420, 1395, 1310, 1235, 695, 660 | 1.44 (s, 3H), 1.51 (s, 3H), 4.28 (s, 1H), 5.50–5.90 (m, 3H), 7.32 (q, 1H), 7.44–7.84 (m, 5H), 8.26 (q, 1H), 8.69 (q, 1H) |
| 2 | 6-Cl-pyrido[2,3-b]pyrazin-2-yl-3-OH | H | | | 3400, 1760, 1630, 1590, 1505, 1435, 1410, 695 | 1.43 (s, 3H), 1.48 (s, 1640, 1H), 5.44–5.88 1430, (m, 3H), 7.28–7.80 (m, 5H), 8.07 (d, 1H), 8.40 (d, 1H) |
| 3 | 6-Cl-pyrido[2,3-b]pyrazin-2-yl-3-OH | OH | | | 3380, 1760, 1630, 1590, 1505, 1435, 1405, 1310, 1230 | 1.42 (s, 3H), 1.46 (s, 3H), 4.21 (s, 1H), 5.38–5.70 (m, 3H), 6.87 (d, 2H), 7.38 (d, 2H), 8.07 (d, 1H), 8.39 (d, 1H) |
| 4 | 6-Br-pyrido[2,3-b]pyrazin-2-yl-3-OH | H | | | 3400, 2910, 1760, 1630, 1500, 1430, 1410, 1310, 1230, 695 | 1.42 (s, 3H), 1.48 (s, 3H), 4.22 (s, 1H), 5.46–5.84 (m, 3H), 7.32–7.72 (m, 5H), 8.09 (d, 1H), 8.43 (d, 1H) |
| 5 | 6-Br-pyrido[2,3-b]pyrazin-2-yl-3-OH | OH | | | 3380, 1760, 1640, 1590, 1500, 1430, 1405, 1310, 1225 | 1.45 (s, 3H), 1.50 (s, 3H), 4.27 (s, 1H), 5.48–5.80 (m, 3H), 7.00 (d, 2H), 7.51 (d, 2H), 8.07 (d, 1H), 8.41 (d, 1H) |
| 6 | pyrimido-pyrazin-2-yl-3-OH | H | 47 | >250 | 3380, 1760, 1640, 1590, 1500, 1445, 1400, 1315, 1260, 695, 660, 585 | 1.44 (s, 3H), 1.56 (s, 3H), 4.24 (s, 1H), 5.44–5.84 (m, 3H), 7.28–7.76 (m, 5H), 9.00 (s, 1H), 9.10 (s, 1H) |
| 7 | pyrimido-pyrazin-2-yl-3-OH | OH | 38 | >250 | 3370, 1760, 1640, 1590, 1500, 1445, 1440, 1310, 1260, 655, 625, 585 | 1.45 (s, 3H), 1.48 (s, 3H), 4.23 (s, 1H), 5.44–5.76 (m, 3H), 6.96 (d, 2H), 7.47 (d, 2H), 9.02 (s, 1H), 9.12 (s, 1H) |
| 8 | 6-Br-7-CH$_3$-pyrido[2,3-b]pyrazin-2-yl-3-OH | H | 58 | >250 | 3380, 1760, 1640, 1600, 1500, 1445, 1390, 1330, 1260, 695 | 1.43 (s, 3H), 1.48 (s, 3H), 2.34 (s, 3H), 4.19 (s, 1H), 5.40–5.64 (m, 3H), 7.20–7.70 (m, 5H), 7.78 (s, 1H) |

TABLE 2-continued

Compound

R—C(=O)—NH—CH(—C₆H₄—R₁)—C(=O)—NH—CH—CH—S—C(CH₃)₂—CH—CO₂K (penicillanate)

| No. | R | R₁ | Yield (%) | m.p. (°C.) | IR (KBr) (cm⁻¹) | NMR (100 MHz) δ(ppm) |
|---|---|---|---|---|---|---|
| 9 | (Br, CH₃-substituted pyrido[2,3-b]pyrazine-OH) | OH | 73 | >250 | 3400, 1760, 1640, 1510, 1395, 1335, 1260 | 1.44 (s, 3H), 1.48 (s, 3H), 2.32 (s, 3H), 4.20 (s, 1H), 5.40–5.74 (m, 3H), 6.92 (d, 2H), 7.40 (d, 2H), 7.68 (s, 1H) |

Having now fully described the invention, it will be apparent to one of ordinary skill in the art that many changes and modifications can be made thereto without departing from the spirit or scope of this invention as set forth herein.

What is claimed as new and intended to be covered by Letters Patent is:

1. A compound having the formula:

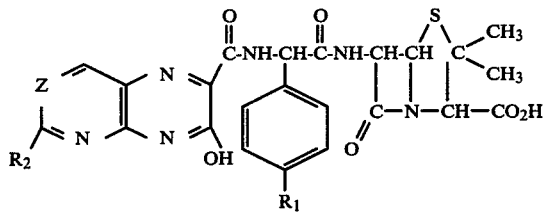

wherein $R_1$ is hydrogen or hydroxy; $R_2$ is hydrogen, methyl or ethyl; and Z is —CH=, —N= or —CX= wherein X is chloro or bromo, or the non-toxic, pharmaceutically acceptable salt thereof.

2. A compound of claim 1, wherein $R_2$ is hydrogen or methyl.

3. A compound having the formula:

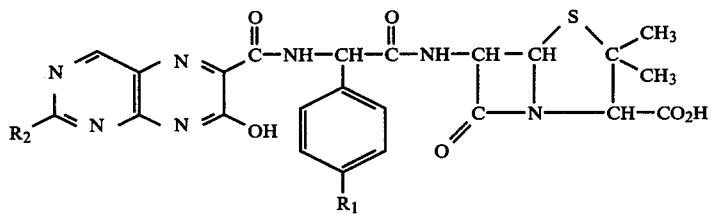

wherein
$R_1$ is hydrogen or hydroxy; and
$R_2$ is hydrogen, methyl or ethyl; or a non-toxic, pharmaceutically acceptable salt thereof.

4. A compound having the formula

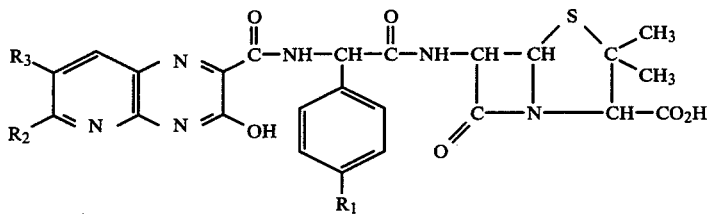

wherein
$R_1$ is hydrogen or hydroxy;
$R_2$ is hydrogen, methyl or ethyl; and
$R_3$ is hydrogen, chloro or bromo; or a non-toxic pharmaceutically acceptable salt thereof.

5. A compound of claim 3, which is 6-[D-2-(7-hydroxypteridine-6-carboxamido)-2-phenylacetamido]penicillanic acid.

6. A compound of claim 3, which is 6-[D-2-(7-hydroxypteridine-6-carboxamido)-2-(p-hydroxyphenyl)acetamido]penicillanic acid.

7. A compound of claim 4, which is 6-[D-2-(3-hydroxypyrido [2,3-b]pyrazine-2-carboxamido)-2-phenylacetamido] penicillanic acid.

8. A compound of claim 4, which is 6-[D-2-(3-hydroxypyrido [2,3-b]pyrazine-2-carboxamido)-2-(p-hydroxyphenyl) acetamido]penicillanic acid.

9. A compound of claim 4, which is 6-[D-2-(3-hydroxy-7-chloropyrido[2,3-b]pyrazine-2-carboxamido)-2-phenylacetamido]penicillanic acid.

10. A compound of claim 4, which is 6-[D-2-(3-hydroxy-7-chloropyrido[2,3-b]pyrazine-2-carboxamido)-2-(p-hydroxyphenyl)acetamido]penicillanic acid.

11. A compound of claim 4, which is 6-[D-2-(3-hydroxy-7-bromopyrido[2,3-b]pyrazine-2-carboxamido)-2-phenylacetamido]penicillanic acid.

12. A compound of claim 4, which is 6-[D-2-(3-hydroxy-7-bromopyrido[2,3-b]pyrazine-2-carboxamido)-2-(p-hydroxyphenyl)acetamido]penicillanic acid.

13. A compound of claim 4, which is 6-[D-2-(3-hydroxy-6-methyl-7-bromopyrido[2,3-b]pyrazine-2-carboxamido)-2-phenylacetamido]penicillanic acid.

14. A compound of claim 4, which is 6-[D-2-(3-hydroxy-6-methyl-7-bromopyrido[2,3-b]pyrazine-2-carboxamido)-2-(p-hydroxyphenyl)acetamido]penicillanic acid.

15. A method of treating a subject suffering from infection by *Pseudomonas aeruginosa* which comprises administering to said subject an effective amount of a compound of claim 1 suitable for retarding said *Pseudonomas aeruginosa*.

16. A method of claim 15, wherein said effective amount is from about 0.1 to 100 mg/kg daily.

* * * * *